(12) United States Patent
Jeng et al.

(10) Patent No.: US 8,129,513 B2
(45) Date of Patent: Mar. 6, 2012

(54) PLANT SENESCENCE-INDUCIBLE PROMOTER

(75) Inventors: Shih-Tong Jeng, Taipei (TW); Pu-Huan Liu, Taipei (TW); Chung-Fu Chu, Taipei (TW)

(73) Assignee: National Taiwan University, Taipei (TW)

( * ) Notice: Subject to any disclaimer, the term of this patent is extended or adjusted under 35 U.S.C. 154(b) by 695 days.

(21) Appl. No.: 12/234,939

(22) Filed: Sep. 22, 2008

(65) Prior Publication Data
US 2009/0241231 A1 Sep. 24, 2009

(30) Foreign Application Priority Data

Mar. 24, 2008 (TW) .............................. 97110308 A

(51) Int. Cl.
*C12N 15/82* (2006.01)
*A01H 5/00* (2006.01)
(52) U.S. Cl. ..................... 536/24.1; 435/320.1; 800/298

(58) Field of Classification Search .................. None
See application file for complete search history.

(56) References Cited

U.S. PATENT DOCUMENTS 5,689,042 A * 11/1997 Amasino et al. ............. 800/298
6,559,357 B1 * 5/2003 Fischer et al. ............... 800/290

OTHER PUBLICATIONS

Liau et al. *Agrobacterium tumefaciens*-mediated transformation of an *Oncidium* orchid. Plant Cell Rep. Jun. 2003;21(10):993-8. Epub Apr. 3, 2003.*
Serek et al. Controlling ethylene responses in flowers at the receptor level. Biotechnol Adv. Jul.-Aug. 2006;24(4):368-81. Epub Apr. 11, 2006.*

* cited by examiner

*Primary Examiner* — Cynthia Collins
(74) *Attorney, Agent, or Firm* — WPAT, P.C.; Anthony King

(57) ABSTRACT

This invention provides a plant senescence-inducible promoter and its relevant recombinant plasmid and transgenic plant.

7 Claims, 2 Drawing Sheets
(1 of 2 Drawing Sheet(s) Filed in Color)

SEQUENCE LISTING

<160> NUMBER OF SEQ ID NOS: 7

<210> SEQ ID NO 1
<211> LENGTH: 32
<212> TYPE: DNA
<213> ORGANISM: Artificial
<220> FEATURE:
<223> OTHER INFORMATION: PCR primer
<220> FEATURE:
<221> NAME/KEY: misc_binding
<222> LOCATION: (1)..(32)

<400> SEQUENCE: 1
acaataagga gaataactca tggaccacct ta                32

<210> SEQ ID NO 2
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc_binding
<222> LOCATION: (1)..(30)

<400> SEQUENCE: 2
ggcataagag gattgggcgg aggaatgatt                30

<210> SEQ ID NO 3
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc_binding
<222> LOCATION: (1)..(30)

<400> SEQUENCE: 3
tatgatagcc agcaaacatt ctggaagttt                30

<210> SEQ ID NO 4
<211> LENGTH: 15
<212> TYPE: DNA
<213> ORGANISM: Artificial
<220> FEATURE:
<223> OTHER INFORMATION: PCR primer
<220> FEATURE:
<221> NAME/KEY: misc_binding
<222> LOCATION: (1)..(15)
<220> FEATURE:
<221> NAME/KEY: misc_feature
<222> LOCATION: (1)..(1)
<223> OTHER INFORMATION: n is a, c, g, or t

<400> SEQUENCE: 4
ntcgastwts gwgtt                15

<210> SEQ ID NO 5
<211> LENGTH: 16
<212> TYPE: DNA
<213> ORGANISM: Artificial
<220> FEATURE:
<223> OTHER INFORMATION: PCR primer
<220> FEATURE:
<221> NAME/KEY: misc_binding
<222> LOCATION: (1)..(16)
<220> FEATURE:
<221> NAME/KEY: misc_feature

```
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 5
ngtcgaswga nawgaa                                                    16

<210> SEQ ID NO 6
<211> LENGTH: 16
<212> TYPE: DNA
<213> ORGANISM: Artificial
<220> FEATURE:
<223> OTHER INFORMATION: PCR primer
<220> FEATURE:
<221> NAME/KEY: misc_binding
<222> LOCATION: (1)..(16)
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 6
wgtgnagwan canaga                                                    16

<210> SEQ ID NO 7
<211> LENGTH: 1352
<212> TYPE: DNA
<213> ORGANISM: Oncidium
<220> FEATURE:
<221> NAME/KEY: promoter
<222> LOCATION: (1)..(1352)

<400> SEQUENCE: 7
aatgccaaga agtagttaag gttttgattg ttaataatac acttattaag aatgcaaata     60
ctattttttg cttgaaccat gagatcatca taaaaattgg cttttatttt acaccttatt   120 ttattttca catgcatggt gatccttcca acaaaaagaa taatattaga attcaataga    180
aattgaaatt aaattatatt accctataag aacatataaa cattagaaaa agcaaggaac   240
taaacccatg tgtgtaattt ggagatcaaa ttatcaaaga gaaagcactc attcccaacg   300
atatggcaaa ttgagaaata aattatacat tatgataagg tcggaggcat gtttgttagg   360
aagttagtta ttactataag gtttggttgc aaggagttca aaagagaagg taataagaag   420
atgataagtg catttttagt atagtagcct tgttgcccac ataattgtct tttattagag   480
tagtaatgag ggggtgtaag agggagataa atttgagaaa tattgacgta aagagcaatg   540
aaatgatttt tggattagta gggaatggaa aaggggtagt gatagtgtcg tgcacatgga   600
tatgatagtt gaataaaggg tagttagatg ataattttgt cttatttaa gttgcatgta    660 agcttcatag ctaatctcca tttcatgcaa ttcattaaaa ataataatag ttttgagtga   720
atgaataact cccggaagta tgttatggtc atcattatcg caacttaaaa attttagatt   780
gggatcctag tgaatgtgta gagtattgag catgagagct cattgataat ggatttagtg   840
gtttaaaaaa ttttatattt aactaatggt tcatttgttt cagctgcacg ttgtagatgt   900
agtaagaaaa ctattttggt gttttttttt attctccaaa aagctatttt tgcatttgga   960
```

```
tgacctgttg tgctaaagaa aaagataaaa attgcttaag ataagctgaa gtaatcgaaa      1020
cctagttgcc tccaacaaat tcaagttatt tgcattaata agaaaaaata gtattgacat      1080
taaaatatga ctatttatta ttagggataa attgcattta ttaaatcaac gtaatctaaa      1140
cttgtagaat gattgcaaaa gaccttttt aatgcttaat attttaacat taactctgta      1200
atcacaatat tttttttata ataaaaatca ttattatggt actctaatta aaaggagtca      1260
aaaatatttt ttactggtgt tgatcttgta agtatttaaa tttacaatta attatcaata      1320
taaatagaag ggaaatgttg aggtataaag gg                                    1352
```

PLANT SENESCENCE-INDUCIBLE PROMOTER

FIELD OF THE INVENTION

This invention relates to a plant senescence-inducible promoter and its relevant recombinant plasmid and transgenic plant.

BACKGROUND OF THE INVENTION

The life of creature, e.g., birth, senescence, disease, and death, is the most interesting and important subject of life sciences. Of the life processes, senescence is a natural part of the development, and eventually causes death of creatures. Thus, with the eventual aim of the retardation of senescence in living organisms, active and extensive research has been and is being conducted on causes and control mechanisms of senescence all over the world. Studies on the control mechanisms of senescence-related genes in plants as well as animals are underway.

Plant senescence is defined as the sequence of biochemical and physiological events in the final stage of plant development. The changes taking place simultaneously or separately in various tissues of a whole plant or in plant tissues such as leaves, flowers or fruits. Plants senescence may be induced by a variety of external factors or stimulators (such as light flux, shading, temperature, water, stress, pathogen attack etc.) as well as internal factors (such as plant growth regulators: ethylene, abscissic acid, cytokinins, auxins etc. and carbohydrate metabolism). When the above condition taking place, a genetic switch is triggered to modify gene expression at the transcriptional and/or post-transcriptional level and induces a change in cell and tissue functions resulting in senescence. If the genes and their regulation regions involved in the induction or retardation of plant senescence are studied and applied in plant science industry, the productivity and economic values can be increased significantly without the environmental destruction caused by the usage of regulatory chemicals.

Furthermore, the promoter used mostly for the gene expression in plant transformation is tobacco mosaic virus 35S promoter that is expressed generally in various tissues and developmental stages of a plant. Hence, tobacco mosaic virus 35S promoter is not suitable for the tissue specific or senescence specific gene expression. It is also not suitable while the general gene expression may cause damage to the plant. Applying a promoter with tissue specificity and developmental stage specificity may be a good solution for the above conditions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1:
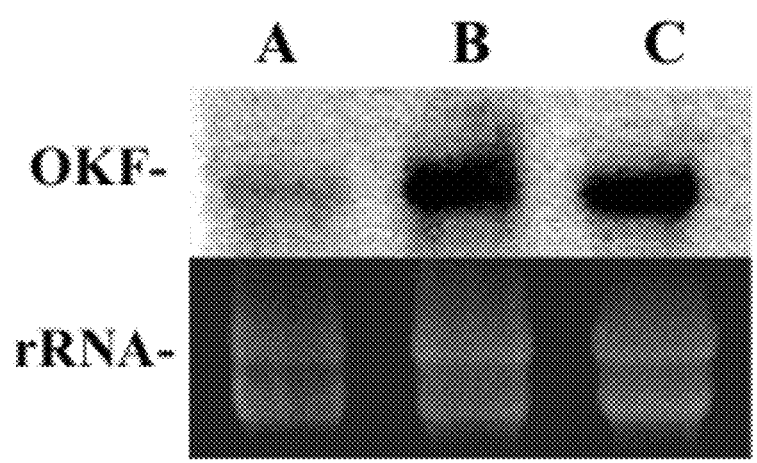
FIG. 1 shows the expression of OKF gene at senescing petal of *Oncidium* analyzed by Western blot analysis. (A) *Oncidium* flower in full bloom; (B) *Oncidium* flower at early stage of senescence; (C) *Oncidium* flower at late stage of senescence; OKF: the position of OKF gene expression; rRNA: the position of ribosome, which indicates the quantity of rRNA participated in the reaction.

This invention provides a plant senescence-inducible promoter and its relevant recombinant plasmid and transgenic plant.

DETAILED DESCRIPTION OF THE INVENTION

During senescence of plant cell, a series of genes are turned on for the operating the senescence program. In the present invention, Suppression Subtractive Hybridization is used for the isolation of gene OKF, which is expressed considerably in the petals of *Oncidium* during petal senescence. POKF, the promoter of gene OKF, is further isolated from the genome of *Oncidium*. The nucleotide sequence of POKF is shown in SEQ ID NO: 7. The POKF promoter has the ability to stimulate the expression of down-stream genes during plant senescence. Thus, the promoter can start the gene expression specifically in plant senescence and can be applied for expressing extrinsic genes in fruits and flowers of crops while these organs enter senescence stage without affecting normal development of the seedlings.

By linking POKF to the target gene and introducing this construct into plants, POKF promoter is able to stimulate the expression of specific target gene during senescence in order to retard plant senescence or change senescence process. This approach can extend the preserve period of fruits or improve the quality and florescence of flowers, and thus increases value added of crops. For instance, *Oncidium* Gower Ramsey is one of the major economic flowers of Taiwan and accounts for more than 90% of imported *Oncidium* cut flowers in Japan; however the vase life of *Oncidium* cut flowers is usually shortened by the production of ethylene caused by the falling of pollinia cap during the process of harvest and packaging. On the other hand, since the harvest season is mainly in late summer, the high temperature also increases the senescence rate of cut flowers. Applying the promoter of the present invention for inducing specifically in flowers the expression of genes which can retard senescence can extend florescence or vase life without affecting the integral physiological condition of the plant. As a result, the economic value of *Oncidium* is increased considerably and the export market is extended as well.

Accordingly, the present invention provides a plant senescence-inducible promoter POKF, which regulates gene expression specifically in plant senescence, comprising a nucleotide sequence of SEQ ID NO: 7. The promoter POKF can further regulate gene expression in specific plant tissues such as tissues in flowers, tissues in leaves, or tissues in fruits.

The said plant of the present invention comprises but not limited to angiosperm. In a preferred embodiment, the plant is Orchid. In a more preferred embodiment, the plant is *Oncidium*.

The present invention also provides a recombinant vector, comprising a nucleotide sequence of SEQ ID NO: 7. The recombinant vector further comprises a target gene, wherein the target gene is expressed specifically in plant senescence. In one embodiment, the target gene can also be expressed in specific plant tissues such as tissues in flowers, tissues in leaves, or tissues in fruits.

The present invention further provides a transgenic plant, containing the said recombinant vector with the promoter POKF. The transgenic plant comprises but not limited to angiosperm. In a preferred embodiment, the transgenic plant is Orchid. In a more preferred embodiment, the transgenic plant is *Oncidium*.

EXAMPLE

The examples below are non-limiting and are merely representative of various aspects and features of the present invention.

The techniques of the present invention represented in the following examples were mainly: isolating senescence-inducible OKF cDNA from *Oncidium* petals by Suppression Subtractive Hybridization after plant senescence; sequencing OKF cDNA; isolating senescence-inducible POKF from *Oncidium* genome using the sequence of OKF cDNA as a reference by Termal Asymmetric Interlaced PCR (TAIL-PCR); analyzing senescence-inducible genes; transforming the promoter POKF into *Arabidopsis thaliana*; and analyzing the expression effect of the promoter POKF in senescence.

Example 1

RNA Extraction

Petals of *Oncidium* were put into a mortar and pestled with liquid nitrogen into powder. 0.1 g petal powder was then well mixed with 0.3 mL TRIZOL (Invitrogen BRL) in a beaker. The well mixed liquid was dispensed into a 2 mL microcentrifuge tube, and after standing at 4° C. for 5 minutes, ⅕ times volume of chloroform/isoamylacohol (24:1) was added and well mixed. After standing at 4° C. for 5 minutes, the mixture was centrifuged at 13000×g for 15 minutes at 4° C. The supernatant was then well mixed with 2 times volume of pre-cooling isopropanol. After standing for 10 minutes at room temperature, the mixture was centrifuged at 13000×g for 10 minutes at 4° C. The supernatant was discarded. The pellet was washed by 0.5 mL of 70% ethanol and then centrifuged at 13000×g for 5 minutes at 4° C. After discarding the supernatant, the microcentrifuge tube with the pellet was inverted to be air-dried for 20 minutes. 20 μL RNA lysis buffer (Protech Technology) was added and vortexed for 15 minutes at 65° C. to re-suspend the pellet. After centrifuging at 13000×g for 5 minutes at 4° C., the supernatant was taken out and reserved in −70° C. refrigerator for later use.

Example 2 mRNA Purification

Dynabeads mRNA purification kit of Dynal brand was used for mRNA purification. 100 μL binding buffer was added to 100 μL total RNA (1 μg/μL). After well mixing, the mixture was heated to 70° C. for 2 minutes and then placed on ice for later use. 200 μL of uniformly suspended Dynabeads containing oligoT25 was transferred into a new microcentrifuge tube and placed on the magnet. The supernatant was removed. The tube was removed from the magnet and the Dynabeads was re-suspended in 100 μL binding buffer. The microcentrifuge tube was placed back on the magnet. After removing the supernatant, the microcentrifuge tube was removed from the magnet and the Dynabeads was re-suspended in 100 μL binding buffer. The Dynabeads and mRNA sample were mixed thoroughly and placed at room temperature for hybridization for 3-5 minutes. After hybridization, the microcentrifuge tube was placed on the magnet for at least 1 minute. The supernatant was removed. The microcentrifuge tube was removed from the magnet and the mRNA-bead complex was washed with 200 μL ice washing buffer. The microcentrifuge tube was placed back on the magnet. After repeating the washing step once, 4 μL of 10 mM Tris-HCL was added. The mixture in the microcentrifuge tube was heated to 65° C. for 2 minutes and then placed on the magnet. The eluted mRNA was transferred to a new PCR tube for later use.

Example 3

Suppression Subtractive Hybridization (SSH)

Clontech PCR-select cDNA subtraction kit was used in the present invention. First-strand cDNA synthesis: 2-4 μL of Poly $A^+$ RNA (2 μg) and 1 μL of cDNA synthesis primer (10 μM) were combined in a 0.5 mL PCR tube. The mixture were heated to 70° C. for 2 minutes and then cooled on ice for 2 minutes. 2 μL 5× first-Strand Buffer, 1 μL dNTP mix (10 mM each), and 1 μL AMV reverse transcriptase (20 unit/μL) were added and well mixed. The tube was incubated at 42° C. for 1.5 hours and then placed on ice immediately for promptly proceeding the second-strand cDNA synthesis.

Second-strand cDNA synthesis: 16 μL 5× second-strand buffer, 1.6 μL dNTP mix (10 mM each), and 4.0 μL 20× second-strand enzyme cocktail were mixed together and added to the product of first-strand cDNA synthesis. The contents were mixed thoroughly and incubated at 16° C. for 2 hours. 2 μL (6 units) T4 DNA polymerase was added. After 30 minutes of incubation at 16° C., 4 μL 20×EDTA/Glycogen was added to terminate second-strand synthesis. 100 μL phenol:chloroform:isoamyl alcohol (25:24:1) was added to the product. After mixing thoroughly, the mixture was centrifuged at 14000×g for 10 minutes at room temperature. The top aquaous layer was collected and placed in a new PCR tube. 100 μL chloroform: isoamyl alcohol (24:1) was added and mixed thoroughly. The mixture was centrifuged at 14000×g for 10 minutes at room temperature. The top aquaous layer was collected and placed in a new PCR tube. 40 μL 4M NH4OAc and 300 μL 95% ethanol were added and mixed thoroughly. The mixture was centrifuged at 14000×g for 20 minutes at room temperature. The supernatant was removed. The pellet was washed with 500 μL of 80% ethanol. The mixture was centrifuged at 14000×g for 10 minutes at room temperature. The supernatant was removed. The pellet was air dried and then dissolved in 50 μL $ddH_2O$. The sample was stored at −20° C. for later use.

Ras I digestion: 43.5 μL ds cDNA, 5.0 μL 10× Ras I restriction buffer, and 1.5 μL Ras I (10 unit/μL) were mixed thoroughly. The mixture was incubated at 37° C. for 1.5 hours. 2.5 μL 20×EDTA/Glycogen was then added to terminated the reaction. 50 μL phenol: chloroform: isoamyl alcohol (25:24:1) was added and mixed thoroughly. The mixture was centrifuged at 14000 rpm for 10 minutes at room temperature. The top aquaous layer was collected, and 50 μL of chloroform:isoamyl alcohol (24:1) was added to it. After mixing thoroughly, the mixture was centrifuged at 14000 rpm for 10 minutes at room temperature. The top aquaous layer was collected, and 25 μL 4M NH4OAc and 187.5 μL 95% ethanol were added to it. After mixing thoroughly, the mixture was centrifuged at 14000 rpm for 20 minutes at room temperature. The supernatant was removed. The pellet was washed with 200 μL of 80% ethanol. The mixture was centrifuged at 14000 rpm for 5 minutes at room temperature. The supernatant was removed. The pellet was air dried and then dissolved in 5.5 μL ddH$_2$O. The sample was stored at −20° C. for later use.

Adaptor ligation: 1 μL of Ras I-digested tester cDNA and 5 μL H$_2$O were mixed and diluted. 2 μL of diluted Ras I-digested tester cDNA, 2 μL of 5× Ligation buffer, 3 μL ddH$_2$O, 1 μL T4 DNA Ligase (400 unit/μL), and 2 μL Adaptor (10 μM) were mixed. Since there were two kinds of adaptors, Adaptor-1 and Adaptor-2R, the mixtures were dispensed into two tubes with different adaptors respectively. The mixtures in tubes were incubated at 16° C. overnight. 1 μL of 20×EDTA/Glycogen was added to terminate the reaction. The sample was heated at 72° C. for 5 minutes and then stored at −20° C.

First hybridization: 1.5 μL of Adaptor-1-Ligate-cDNA (senescence) or 1.5 μL of Adaptor-2R-Ligate-cDNA (senescence) was mixed with 1.5 μL Ras I-digested driver cDNA (un-senescence) and 1.0 μL of 4× hybridization buffer in 0.5 mL PCR tubes. The samples were overlaid with mineral oil. The samples were incubated at 98° C. for 90 seconds and then incubated at 68° C. for 8-12 hours of hybridization. Second hybridization was proceeded immediately after First hybridization.

Second hybridization: The Second hybridization mixture was prepared by mixing 1 μL of 4× hybridization buffer, 1 μL of Ras f-digested driver cDNA (un-senescence), and 2 μL ddH$_2$O together. 4 μL of the Second hybridization mixture was placed in a 0.5-mL PCR tube and overlaid with mineral oil. It was incubated at 98° C. for 90 seconds and then placed on ice. The micropipettor was set at 10 μL (when transferring the sample, it did not be concerned if the mineral oil was transferred, since the mineral oil would still be on the top after centrifugation and would not affect the hybridization at the lower level). 1 μL of Second hybridization mixture was drawn by the micropipettor. The same pipette tip was further used to draw hybridization A-2R-mixture. The entire mixture (containing Second hybridization mixture and hybridization A-2R-mixture) was added to hybridization A-1-mixture and mixed by pipetting up and down. At this moment, hybridization A-1-mixture, hybridization A-2R-mixture, and Second hybridization mixture were all mixed in the same tube. The final mixture was incubated at 68° C. overnight for hybridization. 200 uL dilution buffer was added. After 7-minute of incubation at 68° C., the sample was stored −20° C. After PCR amplification, the product was used for ligation, followed by transformation and colony identification. The identified cDNA was sequenced.

Example 4

Thermal Asymmetric Interlaced PCR (TAIL PCR)

Three specific primers (SP) were designed based on the known cDNA sequence: SP1 (ACAATAAGGAGAATAACTCATGGACCACCTTA), SP2 (GGCATA AGAGGATTGGGCGGAGGAATGATT) and SP3 (TATGATAGCCAGCAAA CATTCTGGAAGTTT). Three arbitrary degenerate (AD) primers were also designed: AD1 (NTC GA(G/C)T(A/T)T(G/C)G(A/T)GTT), AD2 (NGT CGA (G/C)(A/T)G ANA (A/T)GA A), and AD3 ((A/T)GT GNA G(A/T)A NC ANAG A). 1 uL of genomic DNA, 0.6 uL of one of the AD primers (totally three samples), and 0.6 uL of the designed primer SP1, which is closest to the 3' end of the gene, were mixed with 13.7 uL ddH$_2$O, 2 uL of 2.5 mM dNTP, 2 uL of 10×PCR buffer, and 0.1 μL Taq (TaKaRa Taq), totally 20 uL for primary PCR. PCR Program was set as follows: 94° C. for 5 minutes, 42° C. for 1 minutes (2), 72° C. for 2 minutes; 94° C. for 30 seconds, 55° C. for 30 seconds, 72° C. for 100 seconds; go to step (2) for 25 cycles; 72° C. for 7 minutes; end, 4° C. pause. The PCR product was purified by Gel/PCR DNA Fragment Extraction Kit (Geneaid) and dissolved in 15 uL of sterile ddH$_2$O. The solution was 10-fold diluted for use. 1 uL DNA, middle primer SP2, and three AD primers (one for each sample) were used for secondary PCR. PCR Program was as follows: 94° C. for 3 minutes; 94° C. for 30 seconds (2), 55-60° C. for 30 seconds, 72° C. for 100 seconds; go to step (2) for 25 cycles; 72° C. for 7 minutes; end, 4° C. pause. The PCR product was purified by Gel/PCR DNA Fragment Extraction Kit (Geneaid) and 10-fold diluted for use. 1 uL DNA, SP3, the primer closest to the 5' end of the gene, and three AD primers (one for each sample) were used for tertiary PCR. PCR Program was as follows: 94° C. for 3 minutes; 94° C. for 30 seconds (2), 60-65° C. for 30 seconds, 72° C. for 100 seconds; go to step (2) for 25 cycles; 72° C. for 7 minutes; end, 4° C. pause. Analysis of the final PCR product by Agarose gel electrophoresis resulted in one distinct and specific band. The band was cut and purified by Gel/PCR DNA Fragment Extraction Kit (Geneaid). After transformation, culturing and DNA sequencing, the sequence of the promoter POKF was obtained as shown in SEQ IN NO:7.

Example 5

The Expression of Gene OKF at Senescence of *Oncidium* Petal

The RNA of *Oncidium* flower in full bloom, the RNA of *Oncidium* flower at early stage of senescence (creased petal, green pedicel), and the RNA of *Oncidium* flower at late stage of senescence (deep-creased petal, yellow pedicel) were isolated by electrophoresis and then transfected. The RNAs were hybridized with radio-labeled OKF cDNA. The gene expression of OKF at senescence of *Oncidium* petals were analyzed by Northern blot analysis. The result was shown in FIG. 1. Gene OKF was induced for gene expression at senescence of *Oncidium* petals.

Example 6

The Promoter POKF Express Reporter Gene at Senescence of *Arabidopsis*

Figure 2:
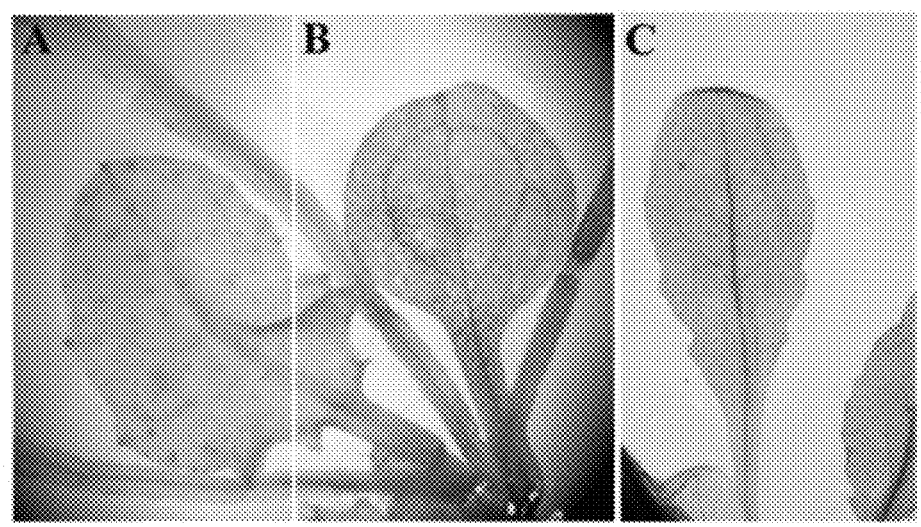
FIG. 2 shows the expression of reporter gene-glucunonidase (GUS) regulated by the promoter POKF in the transformed *Arabidopsis* analyzed by GUS histochemical staining. The promoter POKF, which is OKF gene's promoter, is ligated to the upstream region of the reporter gene GUS, and transformed into *Arabidopsis*. The transformed and non-transformed *Arabidopsis* were then stained. Blue region indicates the position that GUS gene is expressed by POKF. (A) The leaf, which is not senescent, is transparent with blue spot, which indicates few expression of GUS gene. (B) The senescing leaf appears complete blue, indicating that the expresses GUS gene driven by POKF in a great quantity in the senescence stage of plant. (C) The leaf of non-transformed *Arabidopsis* is totally transparent, which indicates that there is no GUS gene expression.

GUS histochemical staining was used to analyze the expression of reporter gene β-glucuronidase (GUS) regulated by the promoter POKF in senescence *Arabidopsis*. The result was showed in FIG. 2. The transformed *Arabidopsis* with GUS gene controlled by the promoter POKF shown, after staining, that the GUS gene was expressed at floral axes, petals, filaments of stamens, and siliques. This proved that the promoter POKF could regulate gene expression at senescence of flower of *Arabidopsis*, which was a Dicotyledon.

While the invention has been described and exemplified in sufficient detail for those skilled in this art to make and use it, various alternatives, modifications, and improvements should be apparent without departing from the spirit and scope of the invention.

What is claimed is:

1. A plant senescence-inducible promoter POKF, comprising the nucleotide sequence of SEQ ID NO: 7.

2. A recombinant vector, comprising the nucleotide sequence of SEQ ID NO: 7.

3. The recombinant vector of claim 2, which further comprises a target gene.

4. A transgenic plant, containing the recombinant vector of claim 2.

5. The transgenic plant of claim 4, which is an angiosperm.

6. The transgenic plant of claim 5, which is an Orchid.

7. The transgenic plant of claim 6, which is an *Oncidium*.

* * * * *